United States Patent
Von Kleinsorgen

(10) Patent No.: US 6,299,899 B1
(45) Date of Patent: Oct. 9, 2001

(54) EXTREMELY FLEXIBLE PLASTER ACTING DERMALLY OR TRANSDERMALLY, AND METHOD FOR PRODUCING SAME

(75) Inventor: Reinhard Von Kleinsorgen, Bendorf (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/331,701

(22) PCT Filed: Nov. 21, 1997

(86) PCT No.: PCT/EP97/06530

§ 371 Date: Jul. 15, 1999

§ 102(e) Date: Jul. 15, 1999

(87) PCT Pub. No.: WO98/29143

PCT Pub. Date: Jul. 9, 1998

(51) Int. Cl.$^7$ ............ A61F 13/02; A61F 13/00; A61K 9/14

(52) U.S. Cl. ............ 424/448; 424/449; 424/486; 424/484; 424/485; 424/487

(58) Field of Search .................. 424/448, 449, 424/486, 484, 485, 487

(56) References Cited

U.S. PATENT DOCUMENTS

| | | |
|---|---|---|
| 3,637,224 | 1/1972 | Triplett et al. .......... 277/229 |
| 4,336,243 * | 6/1982 | Sanvordeker . |
| 4,359,483 * | 11/1982 | Kaetsu et al. . |
| 4,423,099 * | 12/1983 | Muller et al. . |
| 4,559,222 * | 12/1985 | Enscore et al. . |
| 4,617,207 * | 10/1986 | Ueki et al. . |
| 4,624,665 | 11/1986 | Nuwayser .......... 604/307 |
| 4,913,905 | 4/1990 | Fankhauser et al. ...... 424/449 |
| 5,128,124 | 7/1992 | Fankhauser et al. ...... 424/449 |
| 5,194,455 | 3/1993 | Massow et al. .......... 522/152 |
| 5,730,999 * | 3/1998 | Lehmann et al. .......... 424/443 |

FOREIGN PATENT DOCUMENTS

| | | |
|---|---|---|
| 20 06 969 | 2/1970 | (DE) . |
| 39 42 232 A1 | 12/1989 | (DE) . |
| 43 10 012 A1 | 3/1993 | (DE) . |
| 0 114 581 A1 | 12/1983 | (EP) . |
| 0 285 563 B1 | 3/1988 | (EP) . |
| WO 94/14853 | 7/1994 | (WO) . |

* cited by examiner

Primary Examiner—Thurman K. Page
Assistant Examiner—Isis Ghali
(74) Attorney, Agent, or Firm—D. Peter Hochberg; Katherine R. Vieryra; William H. Holt

(57) ABSTRACT

A process for the production of an extremely flexible patch having a dermal or transdermal action and having an adhesive matrix layer which comprises the active compound and is provided with a detachable protective layer on a side facing the skin is characterized in that the matrix layer is not covered on the side facing away from the skin but is given a non-adhesive treatment on its open surface.

3 Claims, No Drawings

EXTREMELY FLEXIBLE PLASTER ACTING DERMALLY OR TRANSDERMALLY, AND METHOD FOR PRODUCING SAME

The present invention relates to an extremely flexible patch having a dermal or transdermal action for controlled release of active compounds to human or animal skin, which comprises an adhesive matrix layer which contains the active compound or compounds and has been freed from its adhesive properties on the side facing away from the skin, and to a process for its production.

Patches for controlled release of active compounds to human or animal skin are adequately known and described as transdermal therapeutic systems (TTS) or "transdermal delivery systems" (TDS). A distinction is generally made in these systems between so-called pouch or reservoir patches and so-called matrix patches, depending on the structure and the nature of the release of active compound. In the first case, such patches comprise a flat pouch or sachet which contains the active compound and of which the side facing away from the skin is impermeable and the side facing the skin is constructed as a control membrane coated with an adhesive for the purpose of adhesion to the skin. Because of their complicated structure, the production of such patches is very expensive, since the individual components have to be prepared separately and then brought together into one system.

Furthermore, because of the necessary thickness of the patch, the wearing properties are impaired. Moreover, with the pouch system there is the risk of so-called "drug dumping", that is to say sudden complete release of the active compound to the skin owing to destruction of the membrane or of the pouch. EP 0 235 563 describes, for example, a transdermal therapeutic system or patch of this type for combined administration of oestrogens and gestagens.

Systems or therapeutic patches which comprise the active compound in microencapsulated form in the reservoir are known from U.S. Pat. No. 4,624,665. The reservoir is embedded between a backing layer and a membrane. The peripheral edge of the patch is provided with a contact adhesive. The structure and the production of such patches are very complicated, since the active compound has to be microencapsulated and distributed homogeneously, to then be embedded between the backing layer and membrane. Furthermore, the patch must be provided with an edge which sticks to skin and covered with a protective layer. Matrix systems or patches generally comprise a backing layer which faces away from the skin and is impermeable to the active compound and an adhesive layer in which the active compound is distributed. To protect the adhesive layer, this is provided with a protective film which has been given an abhesive treatment and must be removed before application. DE-OS 20 06 969, for example, describes such a system in which contraceptive substances are incorporated into the adhesive components or the adhesive film. This specification shows that the adhesive film can be an acrylate.

A disadvantage of known pouch, reservoir or matrix systems or patches is the necessary thickness caused by the production process, which impairs the flexibility in an undesirable manner. The flexibility of the system or patch in fact has a direct effect on its wearing properties, since the wearing comfort required increases with decreasing thickness and decreases with increasing thickness.

The present invention is based on the object of providing a process for the production of an extremely flexible patch which has a dermal or transdermal action, is provided with preferred wearing comfort, dispenses entirely with a separate backing layer and consequently is thinner and more flexible and, as a result of reduced expenditure during production, results in a less expensive alternative to the systems to date.

This object is achieved by a process according to the features of the main claim.

Surprisingly, it has been found that as a result of their greater suppleness, such patches also adhere to skin more reliably and for a longer time.

Because of the comparatively lower thickness and higher flexibility, in contrast to conventional systems or patches the patch according to the invention is also suitable for permanent application to difficult areas of the body, e.g. in the region of the ear, in the genital region or on toenails and fingernails.

A preferred embodiment of a patch according to the invention, given by way of example, is constructed as follows: it comprises a supporting layer, an adhesive part with a non-adhesive surface of a matrix containing the active compound and a detachable protective layer.

To apply the patch according to the invention, the protective layer is removed and the patch is applied to the application area with the aid of the supporting layer such that the adhesive side is facing the skin, and the supporting layer is then peeled off from the side which has been given a non-adhesive treatment.

To cancel the adhesive strength on the surface of adhesive layers, suitable methods are all those which modify the surface structure
a) by changing the molecular bond of the adhesive system in the surface itself
  1. by changing the state of aggregation—liquid/crystalline (influence of heat)
     liquid=adhesive
     crystalline=non-adhesive,
  2. by crosslinking, chemically by crosslinking agents or by radiation, the parts of the polymer molecules which determine the adhesive strength,
b) by changing the surface structure by means of additives which provide a new interface on the outside, are available, additives which can be used being:
  1. solid particles with a particle size in the range of 0.5–20 $\mu$m, which are either spherical or platelet-like in structure. Starch flours or laminar silicates, such as bentonite or mica, may be mentioned as an example. The pulverulent nature of these particles, which allow a uniform application, is decisive.
  2. liquid media which, after application,
     a) form a liquid, semi-solid or solid film physically by themselves —(for example silicone oil, fats, aqueous acrylate dispersions or polymer solutions),
     b) form a new interface by chemical cross-linking.

The adhesive matrix layer can comprise polymers, such as hydroxypropylcellulose, hydroxypropylmethylcellulose, polyvinylpyrrolidone, vinylpyrrolidone/vinyl acetate copolymer 60:40, ethylcellulose, acrylic and methacrylic acid ester copolymers with trimethylammoniummethyl acrylate, copolymers of dimethylaminomethacrylic acid and neutral methacrylic acid esters, shellac, cellulose acetate phthalate, hydroxypropylmethylcellulose phthalate, polymers of methacrylic acid and methacrylic acid esters, ethyl acrylate/methyl methacrylate copolymer 70:30, methacrylic acid/methyl acrylate copolymer 50:50, gelatin, polyvinyl acetate, methacrylate, acrylate dispersions, polyether/polyamide block copolymers, polyethylene/methyl methacrylate block copolymers, polyurethanes, polyester block copolymers, polyisobutylene/styrene/styrene copolymer, styrene/butadiene/styrene/isoprene copolymer, ethylene/vinyl acetate copolymer, polyamide, nitrocellulose and further coat- or film-forming agents which are known to the expert and have at least one reactive polymer end group. The addition of plasticizers results automatically in accordance with the proviso of the required flexibility of the film.

Further substances which may be added or applied to complete a film to be crosslinked are: acrylic- and/or methacrylic-modified polysiloxanes which have a high content of non-polar methyl groups and contain at least one reactive terminal acrylic and/or methacrylic acid group, and furthermore mono-, bi- and trifunctional acrylic and methacrylic acid esters. Vinyl or epoxide compounds containing perfluoroalkyl or perfluoroalkenyl groups or epoxypropylsiloxanes are moreover possible.

Suitable pulverulent substances are additives, in particular, of $SiO_2$, zinc stearate, mica, bismuth oxychloride, titanium dioxide, magnesium oxide, talc, magnesium stearate and other metal salts of fatty acids, and furthermore triglycerides and the colored pigments used in particular in decorative cosmetics. In this connection, it should be noted that the surface of the adhesive matrix layer containing the active compound which faces away from the skin can also be deactivated, for example, by the abovementioned pulverulent foreign substances after application to the skin.

The term "active compound" in connection with the present invention is understood as meaning organic and inorganic chemical substances which can migrate out of the constituents containing them in the device according to the invention and as a result cause a required therapeutic or cosmetic effect. Among the fields of use of the patch according to the invention, human and veterinary medicine and use on plants are of particular importance.

The active compounds to be released are preferably used for dermal treatment of local skin diseases, intra- and transdermal treatment of diseases and wound treatment or skin care in cosmetic formulations.

Local anaesthetics, local antibiotics, antiseptics, antimycotics, antihistamines and antipruritic medicaments, keratolytic agents and cauterizing medicaments, virustatics, antiscabies agents, steroids and various substances for treatment of acne, psoriasis, photodermatitis or precancerous stages are used for dermal treatment of local skin diseases. The active compounds which are administered intradermally include, for example, steroid and non-steroid antirheumatics, local anaesthetics, circulation-promoting substances or vasoprotectors and vasoconstrictors for treatment of vascular diseases, and active compounds for influencing processes in the subcutaneous fatty tissue. Active compounds administered transdermally include, for example, analgesics, antiarrhythmics, narcotics and antagonists thereof, neuroleptics, hormones and hormone replacement substances, antidepressants, tranquillizers, hyponotic agents, psychostimulants, anti-Parkinson agents, ganglion blockers, sympathomimetics, alpha-sympatholytics, beta-sympatholytics, antisympathotonics, antiasthmatics, antiemetics, appetite depressants, diuretics or active compounds for reducing weight and the like.

Preferred active compounds are steroids, such as oestradiol, oestriol, progesterone, norethisterone, norethindrone, levonorgastrel and its-derivatives and ethynodiol diacetate, norgestamate, gestadene, desogestrel, demegestrone, promegestrone, testosterone, hydrocortisone and derivatives thereof; nitro compounds, such as amyl nitrate, nitroglycerine and isosorbide dinitrate; amine compounds, such as nicotine, chlorpheniramine, terfenadine and triprolidine; oxicam derivatives, such as piroxicam; mucopolysaccharidases, such as thiomucase; opiodes, such as buprenorphine, morphine, fentanyl and salts, derivatives or analogues thereof, naloxone, codeine, dihydroergotamine, lysergic acid derivatives, pizotyline, salbutamol and terbutaline; prostaglandins, such as those of the PGA, PGB, PGE and PGF series, such as misoprostol and enprostil, omeprazole and imipramine; benzamides, such as metoclopramine and scopolamine; peptides and growth factors, such as EGF, TGF, PDGF and the like; somatostatin; clonidine; dihydropyridines, such as nifedipine, nitrendipine, verapamil, diltiazem, ephedrine, propranolol, metoprolol and spironolactone; and thiazides, such as hydrochlorothiazide and flunarizine. For wound treatment, haemostatic active compounds and wound-cleaning substances, such as, for example, enzymes, antiseptics, disinfectants and antibiotics, analgesic agents and anaesthetizing active compounds and wound healing-promoting active compounds for stimulating granulation, for inducing vascularization or for promoting epithelialization are employed.

On the other hand, the patch can also be employed for wound treatment for release of oestradiol on chronic wounds, for example ulcera cruris.

In a preferred embodiment for intradermal administration of active compounds, the adhesive layer comprises a eutectic mixture of the local anaesthetics lidocaine and prilocaine. By means of this mixture of active compounds, both for intradermal analgesia before, for example, vein puncture and for treatment of rheumatoid arthritis, an action can be achieved which cannot be achieved with the active compounds and active compound combinations usually employed from the group of topical anaesthetics.

In another preferred embodiment of the patch according to the invention, the film layer comprises plant formulations, such as, for example, extracts or tinctures. These can be used for treatment of local skin diseases, such as, for example, oak bark extract, walnut extract, arnica flower tincture, hamamelis bark extract, ribwort extract, pansy extract or thyme or sage extract, for treatment of damaged and injured skin, such as, for example, St John's wort tincture, sunhat tincture, camomile flower extract or marigold flower tincture, and for care of stressed and damaged skin; such as, for example, birch leaf extract, stinging nettle extract, coltsfoot extract, comfrey tincture, horsetail extract or aloe vera extract. However, plant formulations can also be released from the film layer for intradermal treatment of diseases, such as, for vein conditions, or arnica, marigold and capsicum extracts and tinctures for contusions, sprains or bruises. Plant formulations in the system according to the invention, however, can also be employed in transdermal treatment, thus, for example, ginseng extract for geriatric complaints, valerian tincture, melissa and hop extract for calming in cases of overexcitation, sleep disturbances and stress, cola and tea extracts for achieving a stimulating action or hawthorn extract for stabilizing the circulation.

Another particular embodiment relates to the use of the patch according to the invention as a carrier of narcotics, psychotropic drugs and agents for treatment of Alzheimer's disease and senile dementia. These highly potent medicaments require a system with guaranteed wearing properties for several days.

The following example serves to illustrate a production of a patch according to the invention.

The solution of an adhesive composition containing active compound and comprising

| | |
|---|---:|
| Active compound | 5.0 g |
| Methacrylic acid copolymer | 5.0 g |
| Dimethyl phthalate | 0.25 g |
| Ethyl acetate | 79.75 g | is applied to a siliconized polyester film 100 μm thick (protective layer) and dried at about 80° C. After the drying operation, the resulting laminate passes through a spray tunnel in which magnesium stearate powder is sprayed onto the surface of the adhesive layer (matrix). Magnesium stearate powder which does not adhere to the surface of the matrix layer is removed by a polishing roll.

The matrix surface treated in this way is covered by a siliconized polyester film 30 μm thick (supporting layer).

Transdermal therapeutic patches are stamped out, by known processes, from this laminate which is obtained in this way and comprises protective layer, polymer matrix sprayed with powder and supporting layer.

What is claimed is:

1. An active compound delivering patch formed by a pressure-sensitive adhesive matrix layer containing a pharmacentically active compound for controlled release through an adhesive contact surface of said matrix layer, said adhesive contact surface being covered by a removable protective layer wherein the matrix layer surface facing away from said adhesive contact surface has a non-adhesive property to eliminate the need for a backing layer, without changing the character of the matrix itself.

2. The active compound delivering patch of claim 1 further comprising a removable supporting layer on the side facing away from the adhesive contact surface.

3. The active compound delivering patch of claim 1 having a matrix layer having a thickness to provide high flexibility to said active compound delivering patch.

* * * * *